United States Patent [19]
Siddons et al.

[11] Patent Number: 5,084,397
[45] Date of Patent: Jan. 28, 1992

[54] METHOD AND APPARATUS FOR CONTROLLED REAGENT DEPOSITION IN REACTION CASSETTES AND THE LIKE

[75] Inventors: George Siddons, Elkhart; Frank W. Wogoman, Granger, both of Ind.

[73] Assignee: Miles Inc., Elkhart, Ind.

[21] Appl. No.: 638,101

[22] Filed: Jan. 4, 1991

Related U.S. Application Data

[63] Continuation-in-part of Ser. No. 378,039, Jul. 11, 1989, which is a continuation-in-part of Ser. No. 179,843, Apr. 11, 1988, Pat. No. 4,990,075.

[51] Int. Cl.$^5$ .................................. G01N 21/01
[52] U.S. Cl. ................................... 436/518; 422/57; 422/58; 422/61; 422/99; 435/4; 435/810; 436/165; 436/169; 436/527; 436/531; 436/805; 436/808
[58] Field of Search ................. 422/50, 55–58, 422/61, 99, 101; 436/165, 169, 805, 807, 808, 518, 527, 531; 435/4, 810

[56] References Cited

U.S. PATENT DOCUMENTS 4,977,078 12/1990 Niimuru et al. .................. 435/7

Primary Examiner—Robert J. Hill, Jr.
Assistant Examiner—David Redding
Attorney, Agent, or Firm—Andrew L. Klawitter

[57] ABSTRACT

A method and structure are provided for controlled deposition of liquid analytical reagents on one or more reagent zones disposed in a reaction channel used for performing analytical assay procedures and the like. The substrate surface on which the reaction channel is defined is provided with a unique surface geometry wherein each reagent zone is defined in the form of a sharp, substantially flat, raised portion or mesa-shaped node. The raised node provides a discontinuity in the surface of the reaction channel which is sufficient to prevent a liquid reagent deposited thereon from spreading to adjacent surfaces and, thereby, provides a discrete or localized area to serve as a reagent zone. Controlled deposition is realized since drops of deposited reagent are prevented from spreading uncontrollably over the surrounding substrate surface while, at the same time, allowing the deposited reagent to be completely contacted and removed by the action of a liquid reaction mixture washing the reagent zone. An analytical reagent is incorporated in each such mesa-shaped reagent zone by applying a liquid form of the reagent to the mesa in a controlled manner and subsequently evaporating the liquid portion thereof so as to deposit a dry form of the reagent thereupon.

18 Claims, 1 Drawing Sheet

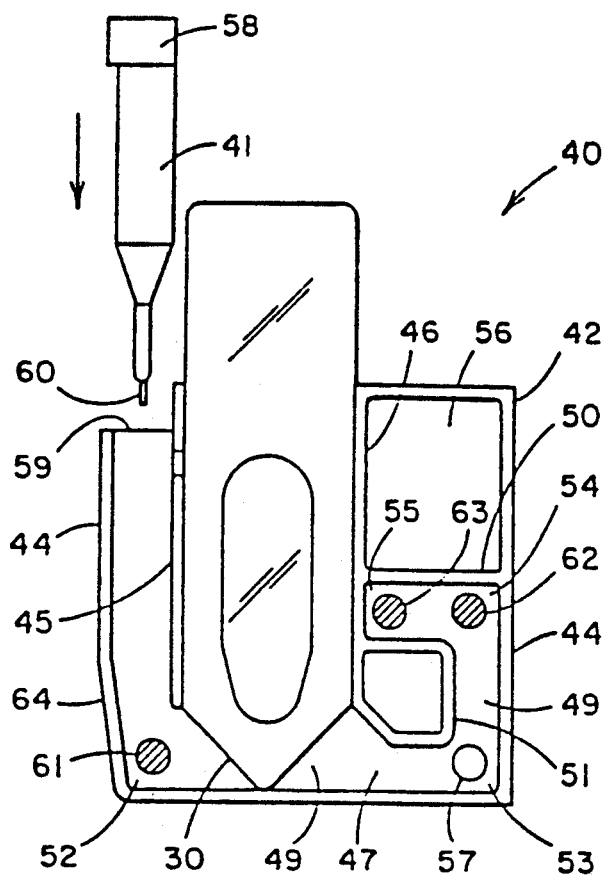
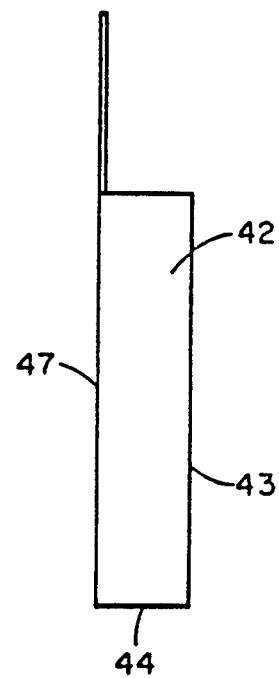
FIG.1  FIG.2
FIG.3
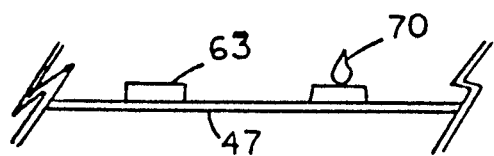

METHOD AND APPARATUS FOR CONTROLLED REAGENT DEPOSITION IN REACTION CASSETTES AND THE LIKE

CROSS-REFERENCE TO RELATED APPLICATION

This is a continuation-in-part of U.S. patent application Ser. No. 378,039, filed July 11, 1989 which, in turn, is a continuation-in-part of U.S. application Ser. No. 179,843, filed Apr. 11, 1988 now U.S. Pat. No. 4,990,075.

BACKGROUND OF THE INVENTION

1. Field of the Invention

This invention generally relates to reaction cassettes and the like used for performing analytical reactions incorporating one or more analytical reagents. More specifically, the present invention relates to controlling the deposition of liquid analytical reagents over discrete reagent zones in such reaction cassettes.

2. Description of the Prior Art

Analytical assay procedures are ubiquitous in a variety of industrial, environmental and medical applications for determination of analytes in sample solutions. Such procedures are employed for determining, inter alia, the amount of an analyte present in a test sample (typically, a liquid reaction mixture or buffer solution) and involve a liquid analytical reaction between the analyte and one or more analytical reagents and which can commonly require a plurality of manipulative steps in order to make the required analytic determination.

Such assay procedures typically involve a number of analytical reactions to be performed sequentially in accordance with a predefined assay protocol and require manipulation of a liquid reaction mixture through a plurality of discrete zones or areas to sequentially contact and react with one or more analytical reagents disposed thereat for realizing various functional steps of the assay.

In realizing self-contained reaction cassettes or vessels particularly adapted to performing analytical assay procedures of the above-noted type, it is important that a specified amount of a liquid reagent be deposited in a controlled manner in specific localized areas in order that the required plurality of discrete reagent zones or areas be defined at appropriate locations within the reaction cassette. Reaction cassettes of this type are provided with a reaction channel which includes the reagent zones disposed at appropriate locations along the channel and adapted to be sequentially contacted by a liquid reaction mixture as it flows along a predefined path in the reaction channel.

The reaction channel is typically defined on a molded plastic substrate having an external surface which is treated to yield a wettable or hydrophilic surface in order to permit the free flow of a liquid therealong. Well-known treatments for rendering such surfaces hydrophilic include plasma treatments such as plasma etching and plasma polymerization, corona discharge, wet chemical treatment, surface coating technologies, and the like.

While the hydrophilic substrate surface permits free flow of the liquid reaction mixture, its very hydrophilic nature poses a significant problem in controlled deposition of liquid analytical reagents at the specific locations where the plurality of reagent zones are defined within the reaction channel. This is because the hydrophilic properties of the surface cause any liquid reagent disposed thereupon to spread in an uncontrollable manner and, accordingly, render the controlled and localized definition of reagent zones extremely difficult.

Attempts have been made to better define the reagent zones by containing the liquid reagent within the zones by means of surface features such as "wells" or "barriers" defined about the confines of the required zones. However, in practical implementations, it becomes necessary that such containment features be extremely shallow in order that the liquid reagents disposed thereupon be capable of being easily contacted and completely removed by the action of a buffer solution, i.e., the liquid reaction mixture, washing over them as the solution flows across the reaction channel where the reagent zones are defined.

These approaches are problematic because the combination of the hydrostatic force produced by the height of the typically single drop of reagent positioned thereupon and the hydrophilic nature of the substrate surface cause the volume of liquid reagent to overcome the necessarily shallow containment barrier and migrate uncontrollably over the reaction channel surface. The controlled deposition of liquid analytical reagent for precise definition of reagent zones is, thus, a difficult, practical aspect of conducting sequential assay procedures.

SUMMARY OF THE INVENTION

In view of the foregoing, it is a primary object of the present invention to provide a structure and method for controlled deposition of liquid analytical reagents on one or more reagent zones disposed in a reaction channel for performing analytical assay procedures and the like.

In this regard, it is also an important object of this invention to provide a structure of the above kind which is adapted to containment of liquid reagent within a specific reagent zone while, at the same time, permitting complete dissolution or resuspension of the liquid reagent as a result of contact with a liquid reaction mixture.

The above and other objects are realized, in accordance with the principles of the present invention, by means of a unique surface geometry for the substrate wherein the reaction channel is defined for performing analytical assay procedures. The unique surface geometry is premised on the fact that sharp edges or abrupt disruptions of surface continuity significantly affect the spread of liquid over a hydrophilic surface. Controlled deposition of liquid reagent is realized by defining the reagent zones in the form of a sharp-cornered deposition area which is raised sufficiently above the surface of the substrate. More specifically, each reagent zone is defined in the form of a substantially flat, raised portion or mesa-shaped node on a selected area of the substrate surface along which the reaction channel is defined.

The advantage with this type of mesa-shaped node is that it provides a discontinuity or break in the surface of the reaction channel sufficient to prevent a liquid (typically a single drop in most assay applications) which is deposited onto the mesa from spreading to adjacent surfaces and, thereby, provides a discrete or localized area to serve as a reagent zone. The use of such a unique surface geometry using mesas for incorporating analytical reagents is particularly applicable and advantageous in reaction cassettes formed of molded plastic substrates. The reagent zones can easily be incorporated into the reaction cassette during the manufacturing process by conveniently molding or otherwise defining one or more mesas at predetermined locations along the reaction channel.

In addition, an analytical reagent can conveniently be incorporated in such a mesa-shaped reagent zone by applying a liquid form of the particular analytical reagent to the mesa and permitting the liquid portion thereof to evaporate and thereby deposit a dry form of the analytical reagent thereupon. The arrangement, accordingly, permits easy and convenient incorporation of analytical reagents prior to device assembly as a result of the controlled deposition of the reagents on each of the mesas.

BRIEF DESCRIPTION OF THE DRAWINGS

Other objects and advantages of the present invention will become apparent upon reading the following detailed description and upon reference to the drawings in which:

FIG. 1 is a front view of an illustrative reaction cassette embodying the unique surface geometry of the present invention, in accordance with a preferred embodiment;

FIG. 2 is a side view of the reaction cassette shown in FIG. 1; and

FIG. 3 is a sectional side view illustrating the mesa-shaped nodes which define the reagent zones according to the principles of the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Referring now to FIGS. 1 and 2, there is shown a self-contained reaction cassette arrangement wherein the unique surface geometry in accordance with the system of the present invention may be advantageously incorporated. Illustrated in these figures is a substantially square reaction cassette or container 40 which is particularly adapted for performing analytical assay procedures involving sequential analytical reactions in a liquid test mixture between an analyte and one or more analytical reagents which react with the analyte to produce a detectable signal.

It will be understood that details pertaining to this type of reaction cassette are described herein only for the purpose of illustrating a particularly advantageous application of the unique surface geometry disclosed and claimed herein; it will be apparent to those skilled in the art, having the benefit of the present disclosure, that the surface geometry and the associated principles disclosed herein may be advantageously applied to other types of devices and mechanisms where controlled deposition of a liquid reagent is desired in discrete or localized areas.

The reaction cassette 40 illustrated at FIGS. 1 and 2 is adapted for performing immunoassays which typically require a number of mixing steps, as well as other cumbersome manipulative steps, such as pipetting and incubation of a test sample and liquid test mixtures. The necessary sequential reagent addition and mixing steps are accomplished within the device by (a) the non-centrifugal rotation of the device at relatively low velocities resulting in the gravitational flow of a liquid mixture to reagent zones or areas in the device designed for performing the various functional steps of the assay, and (b) oscillation of the device to agitate the liquid mixture in contact with flow-disrupting means, such as a corner of the reaction cassette.

The reaction cassette 40 has a substantially horizontal axis of rotation and comprises an open body member 42 which is closed by a lid member 43 in a fluid-tight manner. While the external dimensions of the cassette are not critical, the cassette typically has a height and width roughly between 3 cm and 15 cm and a thickness of between 0.25 cm and 2.0 cm. Particularly preferable dimensions for such a cassette would be a height and width of about 6 cm and thickness of about 1 cm.

The body member 42 and lid member 43 are preferably provided as separate components in order to permit the incorporation of one or more analytical reagents therein prior to assembly of the cassette, as will be described in greater detail below. Once the analytical reagents have been incorporated into body member 42, the member is closed by lid member 43 which is then glued, laser- or sonic-welded or otherwise permanently fastened thereto according to well-known methods in order to realize a fluid-tight seal.

The body member 42 comprises a perimeter side wall 44 and first and second inner walls 45 and 46, respectively, situated on and positioned substantially perpendicular to an outer support wall 47. Side wall 44, together with the contiguous portions to lid member 43 and support wall 47, forms an analytical reaction channel 49, a portion of which is U-shaped and formed by a third inner wall 50 which extends between and substantially perpendicular to second inner wall 46 and side wall 44, and a fourth inner wall 51 which extends from second inner wall 46.

The reaction channel 49 extends around the parameter of side wall 44 and forms first, second, third, and fourth corners 52, 53, 54 and 55, respectively, which provide means for disrupting the flow of a liquid mixture upon agitation in contact therewith, and, in addition, may also serve as viewing zones for detecting and measuring the detectable response provided by a liquid reaction mixture. In particular, first and second corners 52 and 53 are formed by side wall 44 along reaction channel 49. The third corner 54 is formed by side wall 44 and third inner wall 50, and the fourth corner 55 is formed by and between second, third and fourth walls 46, 50 and 51, respectively.

In the embodiment of FIG. 1, a closed area 56 of the reaction cassette 40 is non-functional. However, the third and fourth inner walls 50 and 51 may be removed, modified or otherwise reconfigured to further extend reaction channel 49 into the portion identified as closed area 56. The second corner 53 may be used as a viewing zone by forming lid member 43 and side wall 44 with a substantially transparent cuvette window 57 in corner 53 to permit the accurate measurement of detectable signals in that area.

An inlet port 59 is situated in side wall 44 at the proximal end of reaction channel 49 for introducing a test sample or liquid reaction mixture into reaction channel 49 by means of an appropriate sample introduction device such as a pipette or the like. In a preferred arrangement, introduction of the test sample is realized by means of a capillary holder 41 which comprises a distal end 58 configured to engage with inlet port 59 in the side wall 44 and a proximal end which includes a capillary sampling tube 60. The liquid capacity of capillary tube 60 depends upon the particular analytical assay procedure which is to be performed inside the reaction cassette 40 and the size of the tube 60 will, accordingly, vary in size depending upon the predetermined amount of liquid test sample to be introduced into the cassette 40.

Means other than capillary holder 41 can also be used to introduce a liquid test sample into cassette 40, such as pipets and other liquid delivery means, and inlet port 59 can be stoppered, plugged or otherwise closed subsequent to the introduction of a test sample into the cassette 40 in order to prevent liquid loss during the course of an assay.

According to the principles of the present invention, in order to carry on the sequential analytical assay procedure, one or more analytical reagents are incorporated into reagent zones situated along reaction channel 49, preferably in a dry form, either in areas proximate to or generally between corners 52, 54 and 55. In either case, a liquid disposed in reaction channel 49 can be freely transported by gravity along reaction channel 49 and between corners 52, 53, 54 and 55, by rotating the reaction cassette 40 about the horizontal axis.

More specifically, reagent zones 61, 62 and 63 are situated at first, third and fourth corners 52, 54 and 55, respectively, and are incorporated with analytical reagents for performing a particular analytical assay procedure. The analytical reagents are preferably present in the reagent zones in a substantially dry, water soluble, suspendable or dissolvable form, and can be incorporated along reaction channel 49 according to methods known in the art, such as by noncovalent binding techniques, absorptive techniques, and the like, in the desired order in which they are to be sequentially contacted with a liquid test sample.

It will be understood, of course, that such analytical reagents can be incorporated on or at any surface along reaction channel 49 which will be contacted by a liquid disposed therein. For example, the reagent zones can be situated on a surface of side wall 44, outer wall 47, or an inner surface of lid member 43 at the desired location of a respective reagent zone along reaction channel 49. In some applications, it will be preferable to place reagent zone 63 on the inner surface of lid member 43 opposite the reagent zone 62 on side wall 44. Such disposition of reagent zones 62 and 63 enables essentially simultaneous contact of the incorporated reagents with a liquid mixture transported along reaction channel 49.

In incorporating an analytical reagent within such reagent zones, a liquid form of the particular analytical reagent is first applied to or deposited upon the specific location upon the typically molded substrate on which the reaction channel 49 is defined. Subsequently, the liquid portion thereof is evaporated so as to deposit a dry form of the analytical reagent in the defined location.

As described above, the reaction channel 49 is typically defined on a molded plastic substrate having an external surface which is treated to yield a hydrophilic surface for permitting free flow of liquid therealong. The hydrophilic nature of the substrate surface makes it extremely difficult to control and localize the deposition of liquid analytical reagents at the specific locations where the plurality of reagent zones are defined within the reaction channel. The problem is that the hydrophilic nature of the substrate surface causes any drop(s) of the liquid reagent disposed thereupon to spread over the reaction channel surface in an uncontrollable manner.

The above problem is solved, in accordance with the principles of the present invention, by the provision of a unique surface geometry for the substrate surface which defines the reaction channel in areas where the reagent zones are to be defined. Controlled deposition of liquid reagent is realized by defining the reagent zones in the form of a sharp-cornered deposition area which is raised sufficiently above the surface of the substrate. More specifically, each reagent zone is defined in the form of a substantially flat, raised portion or mesa-shaped node on the surface of a selected area of the reaction channel.

The advantage with this type of mesa-shaped nodes is derived from the fact that sharp edges or abrupt disruptions of surface continuity significantly affect the spread of liquid over a hydrophilic surface. The surface tension of any liquid which is deposited onto the mesa-shaped nodes prevents the liquid from spreading to adjacent surfaces and, thereby, provides a discrete or localized area to serve as a reagent zone.

Unlike the use of surface containment features such as shallow "wells" or "barriers", the use of the slightly raised mesa-shaped nodes does not suffer from the disadvantage that the combination of the hydrostatic force produced by the height of a drop of the liquid reagent and the hydrophilic nature of the surface of the substrate material cause the liquid drop to overcome the containment barrier and migrate uncontrollably over the substrate surface. The surface geometry using the mesa-structures is particularly advantageous in that controlled deposition of liquid analytical reagent is realized in a form which enables the deposited reagent to be completely removed or washed by the action of the liquid reaction mixture as it flows over the reagent zones along the reaction channel.

Referring in particular to FIGS. 1 and 3, a particularly advantageous reagent zone will be in the form of a substantially flat, raised portion or mesa-shaped node disposed on the surface of a selected area of the reaction cassette 40 along reaction channel 49 where a reagent zone is to be defined. An analytical reagent can be incorporated in such a zone by applying a liquid form of the particular analytical reagent (shown in FIG. 3 as a single drop 70) to the mesa and permitting the liquid portion thereof to evaporate to thereby deposit a dry form of the analytical reagent thereto.

The volume of the liquid form of the analytical reagent will depend, of course, upon the surface area of the mesa, and will preferably be from between about 0.002 mL and about 0.1 mL, and more preferably from between about 0.005 mL and about 0.015 mL. As described above and as will be understood by one skilled in the art, the surface discontinuity or break provided by the raised mesa will prevent a liquid (usually aqueous, and usually comprising water as its principal solvent component) which is deposited onto such a mesa from spreading to adjacent surfaces and thereby provides a discrete or localized area to serve as a reagent zone.

The height, shape and other dimensions of the raised node of the present invention can vary according to the particulars of the analytical device involved. Normally, however, the most important parameter is the height of the node, i.e., the distance that the node is raised from the substrate surface that forms the reaction channel, since it is this feature which prevents the uncontrolled movement of a deposited liquid reagent. The raised upper surface of the node is preferably at least about 0.005 inch away from the reaction channel surface. The allowable upper limit of the height of the node will be dependent on other factors, such as the height of the volume of liquid reaction mixture that flows along the reaction channel, the degree of disruption of the flow of such liquid mixture along the channel that can be tolerated or that is desired, and the like. It has been found for the typical cassette devices described herein that nodes extending less than about 0.015 inch from the channel surface are advantageous.

The surface area of the raised upper surface of the node can also vary widely and is principally dependent on volume and physical properties (e.g., surface tension, viscosity, etc.) of the liquid reagent to be applied. Likewise, the perimetric shape of the raised surface can be varied and selected in order to provide the most desirable properties. For instance, square, rectangular, hexagonal, octagonal, and like shapes can be used. Preferably, the raised surface is circular or ellipsoidal, with circular surfaces having an area about 0.2 inch being of particular advantage. A reaction cassette having a circular mesa-shaped node of about 0.188 inch in surface area has been tested and found to be particularly effective in realizing the purposes described above.

The use of the above-noted type of mesa-shaped structure to define a reagent zone and incorporate an analytical reagent thereupon is particularly useful during the manufacturing processes involved with the above-described type of reaction cassette. This is because the cassette 40 can be easily molded or otherwise manufactured with one or more mesas at predetermined locations which can serve as reagent zones, and, accordingly, easy and convenient incorporation of analytical reagents is possible prior to assembly of the reaction cassette 40.

It will be apparent from the foregoing that the present invention provides a unique surface geometry using mesa-shaped structures to define analytical reagent zones which are particularly adapted to controlled deposition of liquid analytical reagent thereupon. The arrangement is such that controlled deposition is realized in a manner which prevents drops of deposited reagent from spreading uncontrollably over the surrounding substrate surface in the reaction channel where the reagent zones are defined while, at the same time, allowing the deposited reagent to be completely contacted and removed by the action of a buffer solution washing over the reagent zones.

It will be evident that the present invention can be applied to a wide variety of analytical devices and cassettes. The particularly useful cassette described in detail above as an illustrative embodiment is adapted for use in applications wherein a liquid reaction mixture is transported along the reaction channel by gravitational flow. In such implementations, liquid transport is effectively obtained by the simple means of rotating the device about a horizontal axis at a speed which produces no substantial centrifugal force. However, it should be noted that the advantageous features of the present invention can also be incorporated in devices wherein liquid flow is affected by means other than, or in addition to, gravity, such as by application of centrifugal force, use of vacuum or liquid pumps, and so forth.

While this type of surface geometry has been described above in connection with a preferred arrangement wherein reagent zones using the mesa-shaped nodes are defined in the reaction channel for a self-contained reaction cassette, it will be understood that this type of geometry is applicable to and can conveniently be used in a variety of other applications where controlled deposition of a liquid reagent is desired within one or more highly localized reagent zones or areas.

We claim:

1. A method for controlled deposition of an analytical reagent at a reagent zone positioned along a reaction channel wherein an analytical reaction is performed by causing a liquid reaction mixture to contact a discrete reagent zone having an analytical reagent disposed thereat, the reaction channel being defined about a substrate having a hydrophilic surface, the method comprising the steps of:

providing said reagent zone in the form of a node extending away from said substrate surface about which said reaction channel is provided, and said node constructed so as to provide a substantially horizontal upper surface constructed to support a volume of liquid thereupon, and depositing a predetermined amount of said liquid analytical reagent on said horizontal surface of said node defining said reagent zone, whereby the surface tension of said liquid reagent on said node prevents said liquid from spreading away from said node to adjacent sections of said substrate surface and thereby permits controlled deposition of said liquid reagent on said reagent zone.

2. The controlled deposition method according to claim 1 further including the step of evaporating the liquid portion of said analytical reagent deposited upon said reagent zone thereby depositing a dry form of said analytical reagent thereupon.

3. The controlled deposition method according to claim 1 wherein said reagent zone is constructed in the form of a mesa-shaped node providing said substantially horizontal upper surface.

4. The controlled deposition method according to claim 3 wherein said horizontal upper surface of said mesa-shaped node has a surface area constructed to support thereupon a volume of between about 0.002 mL and about 0.1 mL of said liquid analytical reagent.

5. In a reaction cassette for performing an assay involving an analytical reaction between one or more components of a liquid test mixture and an analytical reagent, the cassette comprising a reaction channel along which the liquid test mixture is manipulated to contact and react with said analytical reagent disposed at a corresponding reagent zone, the improvement comprising:

said reagent zone being constructed in the form of a node extending away from the surface of said reaction channel said node constructed so as to provide a substantially flat upper surface parallel to said surface of said reaction channeled having positioned thereupon a predetermined amount of a dried analytical reagent.

6. The improved reaction cassette as set forth in claim 5 wherein said reagent has been positioned on said upper surface of said node by (i) depositing a predetermined volume of said reagent in liquid form on upper surface of said node in a controlled fashion, said node constructed so as to provide a break in the surface of the reaction channel sufficient to prevent the liquid reagent from spreading away from said node to said reaction channel surface adjacent thereto, and (ii) subsequently evaporating the liquid portion thereof.

7. The improved reaction cassette as set forth in claim 5 wherein said reagent zone is constructed in the form of a mesa-shaped node providing said substantially flat upper surface parallel to said surface of said reaction channel.

8. The improved reaction cassette as set forth in claim 7 wherein said node is positioned along said reaction channel in such a manner that said analytical reagent positioned thereupon is contacted and completely removed as said liquid test mixture contacts said reagent zone.

9. The improved reaction cassette as set forth in claim 7 wherein said flat upper surface of said mesa-shaped node is constructed such that said surface stands at least about 0.005 inch from the surface of said reaction channel.

10. The improved reaction cassette as set forth in claim 7 wherein said substantially flat upper surface is constructed to provide a surface area to support thereupon a volume of between about 0.002 mL and about 0.1 mL of said liquid analytical reagent.

11. An analytical reaction cassette for performing an analytical reaction to determine an analyte in a liquid test sample, the cassette comprising:
  (1) inlet means for introducing a liquid test sample into said reaction cassette;
  (2) a reaction channel in liquid communication with said inlet means; and
  (3) at least one reagent zone positioned along said reaction channel and comprising an analytical reagent which interacts with said analyte to produce a detectable response as a function of the analyte,
  said reagent zone constructed in the form of a mesa-shaped node positioned along said reaction channel, said node comprising a substantially flat upper surface parallel to said surface of said reaction channel when said upper surface of said mesa is positioned horizontally, whereby the surface tension of a liquid deposited onto said upper surface prevents the liquid from spreading to adjacent surfaces on said channel and thereby provides a localized area to serve as a reagent zone.

12. The analytical reaction cassette according to claim 11 comprising at least two said reagent zones positioned along said reaction channel in such a way that said liquid test sample can sequentially be brought into contact therewith.

13. The analytical reaction cassette according to claim 11 wherein each of said mesa-shaped nodes corresponding to said reagent zones has an analytical reagent positioned thereupon by applying a liquid form of said analytical reagent to said upper surface of said mesa and permitting the liquid portion thereof to evaporate, thereby depositing a dry form of the analytical reagent thereupon.

14. The analytical reaction cassette according to claim 13 wherein said substantially flat upper surface is constructed to a surface area to support thereupon a volume of between about 0.002 mL and about 0.1 mL of said liquid analytical reagent.

15. A method of controlled deposition of liquid analytical reagent onto localized areas or reagent zones positioned along a reaction channel in a reaction cassette for performing analytical reactions, said method comprising the steps of:
  providing each reagent zone in the form of a substantially horizontal, mesa-shaped node on the surface of said reaction channel, and
  depositing a predetermined volume of said analytical reagent in liquid form onto said upper surface of said node, whereby the surface tension of said liquid reagent deposited onto said node prevents said liquid reagent from spreading to surfaces adjacent said node.

16. The controlled deposition method as set forth in claim 15 wherein said upper surface of said mesa-shaped node is constructed such that said surface stands at least about 0.005 inch from the surface of said reaction channel.

17. The controlled deposition method according to claim 15 wherein said substantially flat upper surface is constructed to provide a surface area to support thereupon a volume of between about 0.002 mL and about 0.1 mL of said liquid analytical reagent.

18. The controlled deposition method according to claim 15 wherein the liquid portion of said liquid analytical reagent deposited on said upper surface of said mesa-shaped node is evaporated to thereby deposit a dry form of said analytical reagent thereupon.

* * * * *